United States Patent [19]  [11] 3,986,764
Torburn  [45] Oct. 19, 1976

[54] PANEL FOR SUPPORTING A PAIR OF ELONGATED MATING CONNECTORS AND SELECTIVELY LOCKING THEM TOGETHER

[75] Inventor: Roy B. Torburn, San Carlos, Calif.

[73] Assignee: GTE Automatic Electric Laboratories Incorporated, Northlake, Ill.

[22] Filed: Mar. 31, 1975

[21] Appl. No.: 563,757

[52] U.S. Cl. .................. 339/75 M; 339/119 R; 339/274
[51] Int. Cl.² ................ H01R 13/60; H01R 13/54
[58] Field of Search ................... 339/39, 75–77, 339/119–121, 198, 274; 24/248 E

[56] References Cited
UNITED STATES PATENTS

| | | | |
|---|---|---|---|
| 1,549,437 | 8/1925 | Bissell | 339/75 R |
| 1,754,053 | 4/1930 | Schlaegel | 339/239 |
| 2,242,545 | 5/1941 | Randolph | 24/248 E |
| 2,801,394 | 7/1957 | Derner et al. | 339/274 |
| 2,871,457 | 1/1959 | Jencks | 339/75 M |
| 3,820,056 | 6/1974 | Ayer | 339/198 R |

FOREIGN PATENTS OR APPLICATIONS 729,296  5/1955  United Kingdom ............. 339/75 M Primary Examiner—Roy Lake
Assistant Examiner—Neil Abrams
Attorney, Agent, or Firm—Russell A. Cannon; Leonard R. Cool

[57] ABSTRACT

A panel for selectively locking pairs of elongated mating connectors together in a connected relationship including a pair of symmetrically shaped plates that are rigidly supported in a spaced-apart and parallel relationship by a pair of channels extending therebetween. One connector of each pair is rigidly attached to first legs of the two channels by screws. The other connector of each pair is plugged into an associated one connector and has an elongated surface that is spaced from the latter. Generally rectangularly shaped holes in the plates are positioned and shaped to receive the ends of a locking bar and support it between the plates such that rotation of the bar in one direction provides over-center cam action which forces the bar into contact with the elongated surfaces of the other connectors to hold them in place. Disconnection of connectors is accomplished by rotating the locking bar in the opposite direction and removing a second connector from a first connector and the panel. The ends of the locking bar are bent over parallel to the plates in order to keep the bar from slipping out of the openings. Slots in the front of the plates extend into the openings so that the locking bar may be removed therefrom.

7 Claims, 7 Drawing Figures

PANEL FOR SUPPORTING A PAIR OF ELONGATED MATING CONNECTORS AND SELECTIVELY LOCKING THEM TOGETHER

BACKGROUND OF INVENTION

This invention relates to structure for locking a pair of elongated multipin mating connectors together, and more particularly to rack-mounted panel structure in a telephone office for supporting pairs of telephone-type 52-pin mating ribbon connectors with convenient mechanism for locking the pairs of connectors together and selectively providing convenient access to individual pairs of connectors.

In a telephone central office, it is necessary to interconnect large numbers of points at one location with corresponding points at another location. Such interconnections are accomplished with jumper cables and pairs of mating multipin ribbon connectors. The points at each location are wired to corresponding pins on associated 52-pin ribbon connectors which may, for example, be model 57-10500-14 connectors that are manufactured by TRW/Cinch Connectors, Elk Grove Village, Ill. Jumper cables containing a plurality of cable pairs, e.g., 26 each, therein are threaded between the two locations. The wires at each end of the jumper cables are connected to corresponding pins of associated mating 52-pin ribbon connectors which may, for example, be model 57-20500-7 connectors manufactured by TRW/Cinch Connectors of Elk Grove Village, Ill. The interconnection is completed by pressing the mating connectors together and threading locking screws through flanges thereon and into the body of the other connector. The assembled connectors are then left hanging on the jumper cable, for example in a main distribution frame. This technique does not provide support for the connectors and requires access to both sides of a connector pair to reach the locking screws.

An object of this invention is the provision of structure for supporting and selectively locking together a pair of mating connectors in a connected relationship.

DESCRIPTION OF DRAWINGS

This invention will be more fully understood from the following detailed description thereof, together with the drawings wherein.

DESCRIPTION OF PREFERRED EMBODIMENTS

Figure 1:
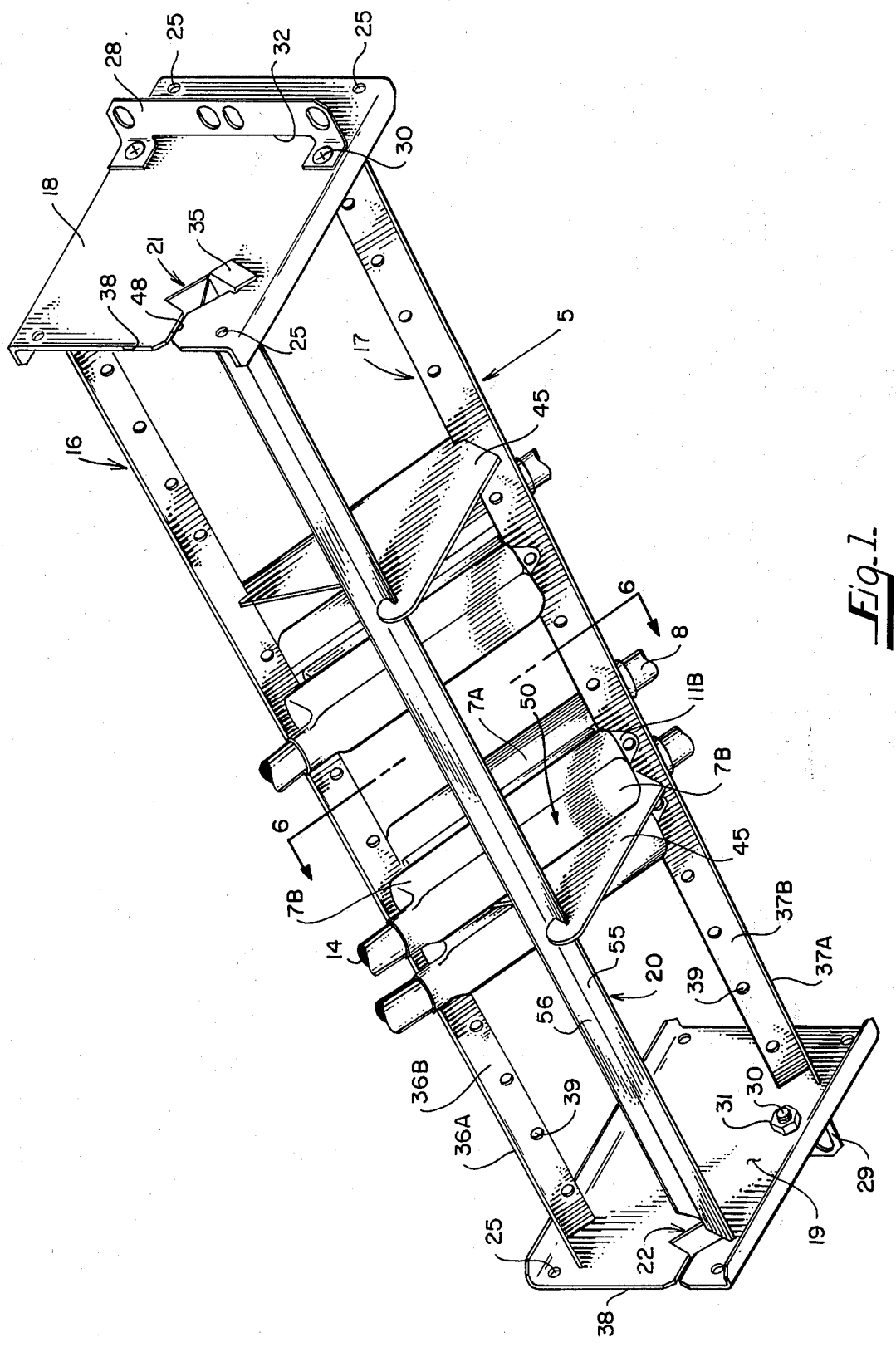
FIG. 1 is a perspective view, looking up at the bottom and front, of a panel 5 embodying this invention from the right side thereof.

Refer now to the perspective view, looking toward the bottom and front, of a preferred embodiment of a panel 5 embodying this invention in FIG. 1. This panel is employed to secure pairs of mating connectors such as the connectors 7A and 7B in a connected relationship. Although only one pair of connectors is specifically discussed, a plurality of connector pairs can be secured in the panel in the same manner. The connectors 7A and 7B are shown in more detail in the section views in FIGS. 6 and 7. The connector 7A is associated with cable 8 and comprises a base 9A in a cover that is attached to the cable 8 by a screw 10A (see FIG. 6). The connector 7A has on one end thereof a flange 11A with a hole therethrough, and has in the other end thereof a threaded hole 12A. The base 9A has a plurality of pins (not shown) depending therefrom that are connected to wires of the cable 8. The other connector 7B, which is associated with cable 14, is similar to the connector 7A and has corresponding elements which are designated by the same reference numerals and the letter B (see FIG. 7).

Again referring to FIG. 1, this panel 5 comprises a pair of elongated support members 16 and 17 that are rigidly secured to a pair of channel-shaped end plates 18 and 19, and a locking bar 20 that is located in the openings 21 and 22 in associated end plates 18 and 19. The shape of the openings 21 and 22 is shown more clearly in FIG. 2. In a panel that was built and operated, support members 16 and 17 were welded to the end plates 18 and 19. Alternatively, the ends of one of the legs of the members 16 and 17 may be foreshortened and the ends of the other legs bent over at 90° and bolted to the end plates. A plurality of threaded holes 25 extend through the plates 18 and 19 near the tops and bottoms thereof. Right-angle brackets 28 and 29 are mounted on the exteriors of the plates 18 and 19 by screws 30 and nuts 31 for attaching the panel to a rack (not shown) in a telephone office. When the brackets 28 and 29 are near the back of the end plates 18 and 19, the panel 5 extends out in front of a rack. When these brackets 28 and 29 are mounted with holes 25 at the front of the plates, the panel 5 may be flush with the front of a rack. Recesses or cutouts 35 are formed in the brackets 28 and 29 for providing spaces between the outside surfaces of plates 18 and 19 and the central elongated portions of the associated bracket. These spaces or openings are sufficient to enable the tabs 35 on the locking member 20 to pass between the outer surfaces of the plates and the brackets when the latter are mounted in holes 25 at the front of the plates.

Figure 3:
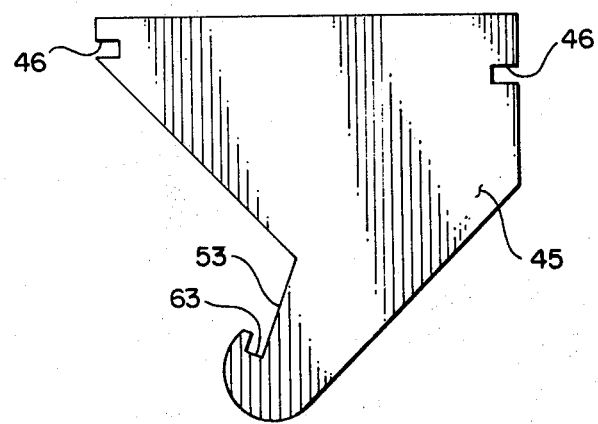
FIG. 3 is a side view of a rib 45 in the panel 5 in FIG. 1.

The support members 16 and 17 have right-angle cross sections with legs 36A and 37A that are parallel to each other and legs 36B and 37B having surfaces thereof in parallel planes that are spaced apart by the thickness of the flanges 11A and 11B on the ends of the connectors. These planes that are parallel to the surfaces of legs 36B and 37B form an acute angle with respect to the fronts 38 of the end plates. A plurality of holes 39 which extend through the legs 36B and 37B are spaced apart a distance that is slightly greater than the thickness of the ribbon connectors 7A and 7B. One connector 7A of each pair is mounted on the support members 16 and 17. The flange 11A preferably extends under the leg 36B of member 16 with the other end of the connector 7A above the leg 37B of member 17 (see FIG. 6). This connector 7A is secured to the members 17 and 18 by screws 41 and 42 and a nut 43. A pair of ribs 45 may be attached to the support members 16 and 17 to provide additional strength to prevent twisting of the panel. The ribs 45 are shown in detail in FIG. 3 and have notches 46 that fit over the legs 36B and 37B of the supports and are welded thereto.

Figure 2:
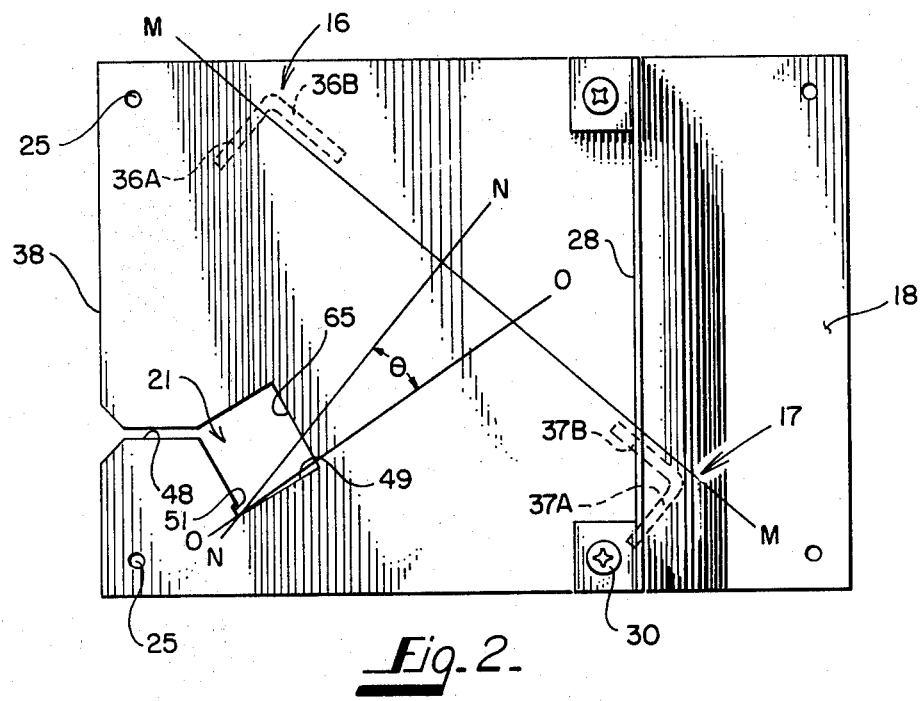
FIG. 2 is a right-side view of the panel 5 in FIG. 1, with the locking member 20 removed therefrom.
Figure 6:
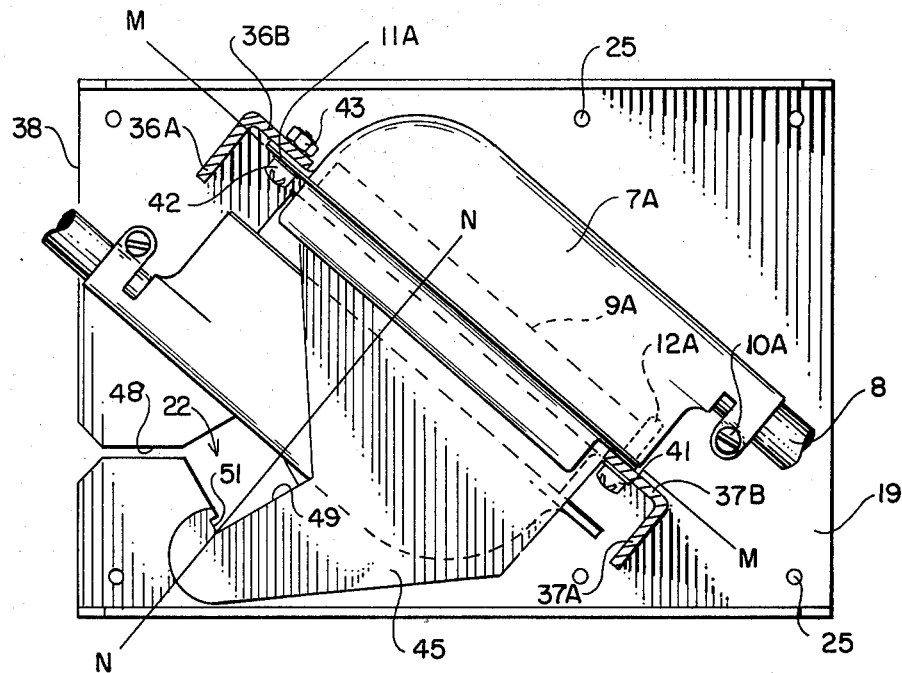
FIG. 6 is a section view of the panel 5 taken along lines 6 — 6 in FIG. 1 with the connector 7B and the locking member 20 removed for purposes of illustration.
Figure 7:
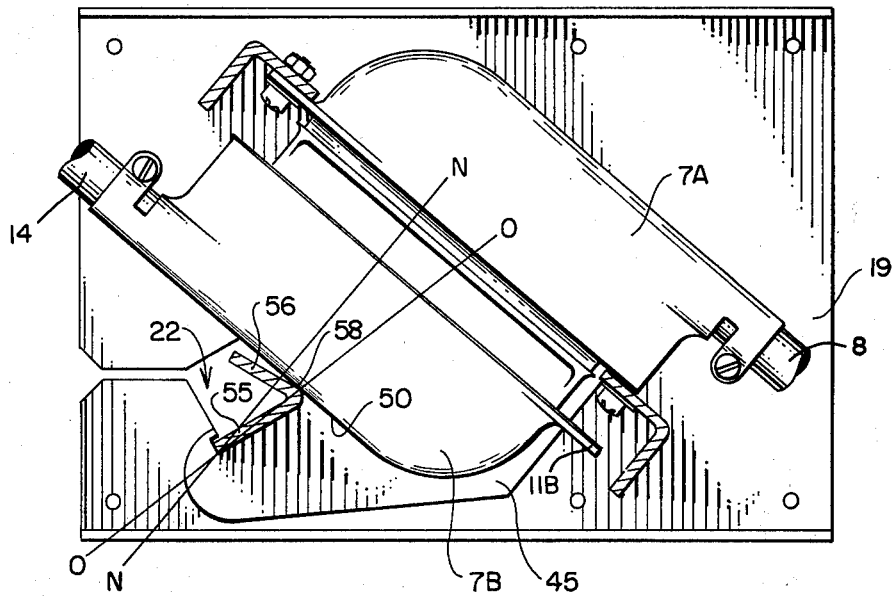
FIG. 7 is a section view of the panel 5 taken along lines 6 — 6 in FIG. 1 with the locking member 20 contacting the back 50 of connector 7B to lock it in place.

A slot 48 in the front of the end plate 18 extends into the opening 21 which was rectangularly shaped in the panel that was built and operated (see FIG. 2). The side 49 of the opening 21 forms an acute angle with respect to the line N — N that is perpendicular to the line M — M, which is parallel to the back 50 of connector 7B. A notch 51 is formed in the side of the opening 21 that is spaced away from the line M — M. The opening 22 in plate 19 has a similar shape. The sides 53 of the ribs 45 are preferably aligned with the sides 49 of the openings. These openings 21 and 22 are positioned with respect to the line M — M such that the back 50 of a connector 7B extends over these openings 21 and 22 when the connectors 7A and 7B are positioned in the panel as is shown in FIGS. 6 and 7.

Figure 4:
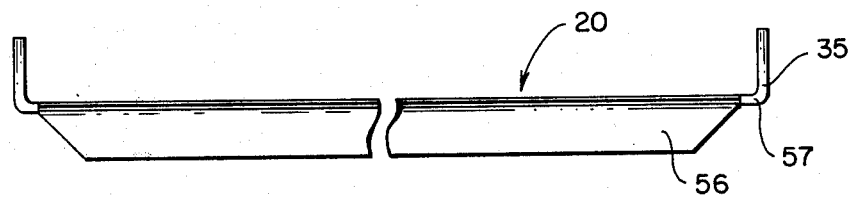
FIG. 4 is a top view of the locking member 20.
Figure 5:
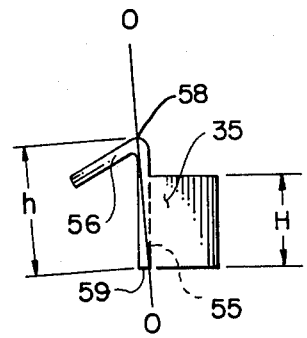
FIG. 5 is a right-side view of the locking member 20.

The locking member 20 is shown in detail in the top and end views thereof in FIGS. 4 and 5. It is formed from an elongated strip of metal that is bent to provide an angularly shaped cross section having legs 55 and 56 that form an acute angle. The ends of the longer leg 55 are also bent at 90° to form the tabs 35 which bear on the plates 18 and 19 to keep the locking member 20 from sliding sideways when it is located in the openings 21 and 22. The height H of the shoulders 57 on the leg 55 is less than the length and width of the openings 21 and 22 to enable the member 20 to rotate freely in these openings. The slant height h of member 20 is selected such that the top 58 thereof contacts the back 50 of connector 7B when the back of leg 55 is against the sides 49 of openings 21 and 22 and the sides 53 of the ribs 45, with the connectors 7A and 7B positioned in the panel as is shown in FIGS. 6 and 7.

In operation, the brackets 28 and 29 are employed to mount the panel 5, for example, on a rack (not shown). The locking member 20 may be removed from the panel while connector 7A, or as many thereof as may be desired, is secured to the support members 16 and 17 by screws 41 and 42 and nut 43 (see FIG. 6). The mating connector 7B is plugged into associated connector 7A. The locking member 20 is then positioned with the top 58 thereof extending toward the connector 7B and passed through the slots 48 and into the openings 21 and 22 in the end plates. With the bottom 59 of the locking member 20 in the notches 51 in the end plates and in the notches 63 in the ribs, the member 20 is rotated so that the top 58 thereof contacts the back 50 of connector 7B along the line N — N which is orthogonal thereto. Rotation of member 20 is continued past this line N — N until the leg 55 contacts the sides 49 of the openings 21 and 22. At this point, the line O — O through the locking member is past the normal N — N and the member 20 is locked in this position between the notch 51 and side 49 of the openings, with the top 58 against the back 50 of connector 7B, to maintain the connectors 7A and 7B in a connected relationship. This over-center cam action of the member 20 provides a convenient mechanism for holding connectors in this connected position. The size and shape of the rectangular openings 21 and 22 is preferably such that the locking member 20 may be rotated away from the back 50 of connector 7B and left in these openings while connectors 7B are attached or disconnected from associated connectors 7A. Alternatively, the member 20 may be easily removed from and inserted into the openings 21 and 22 for working with connectors.

It was determined empirically on the test model of a panel 5 that the over-center cam action of locking member 20 operated optimally with the angle $\theta$ in FIG. 2 between 10° and 15°. The magnitude of this angle may vary somewhat depending on the spacing of the back 50 of connector 7B and the notch 51 as well as the shape of the cross section of locking member 20.

Although this invention is described in relation to a preferred embodiment thereof, obvious modifications and variations thereof will be apparent to those skilled in the art without departing from the spirit and scope of this invention. By way of example, the angularly shaped locking member 20 may be a locking bar where opposite edges thereof are in the notches 51 in the opening and contact the back 50 of connector 7B. Also, the openings 21 and 22 may be other than rectangularly shaped. Further, the notch 51 may be other than adjacent the side 49 of the openings and can be a protrusion rather than a notch. Similarly, the stop for locking member 20 that cooperates with the notch 51 may be a protrusion in the edge 65 of the openings rather than the sides 49 thereof. Also, by properly locating the stops in the openings 21 and 22, the over-center cam action may be obtained by rotating the member either clockwise or counterclockwise in FIG. 7. Further, it is possible to form the frame of the panel 5, except for the locking member 20, from a single plate or sheet of metal. This is readily accomplished by stamping the plate to a designated exterior shape (which would not look like the outline of shelf 5, but which would accomplish the same result) and to form openings between pieces of metal representing legs 36B and 37B of the support members 16 and 17 as well as the openings 21 and 22 and associated slots 48. The ends of the plate can then be bent at 90° to form sides representing the end plates 18 and 19. Finally, the ends of the newly formed sides of this plate can be bent at 90° along the openings 21 and 22 and slots 48 to form the brackets 28 and 29. A locking member 20 will then fit into the slots 48 and openings 21 and 22 stamped into the plate. The scope of this invention is therefore determined by the appended claims, rather than from the above detailed description of a preferred embodiment thereof.

I claim:

1. A panel for supporting pairs of first and second mating connectors having elongated bodies and for selectively locking a plurality of connector pairs in a connected relationship, comprising:
   a pair of plates that are spaced apart, are parallel to each other, and have surfaces that face each other, each of said facing surfaces having an opening therein;
   first means which is a support means extending between and rigidly secured to said plates for having first connectors attached thereto, second connectors being plugged into associated first connectors,
   an elongated locking member having opposite ends thereof in associated ones of said openings in said plates;
   second means including the openings in said plates for rotatably supporting said locking member between said plates for rotation of said locking member about a first line therethrough, with said locking member adjacent surfaces of the second connectors that are spaced from associated first connectors,
   the line of rotation which is the first line of said locking member having a second line through a first point on the first line, the second line being substantially normal to a plane containing the surfaces of the second connectors at a second point on the surface of one of said second connectors; said locking member also having a third point on the surface thereof that is radially spaced away from said first point; said locking member being rotated about the first line to cause the third point on the former to make pressure contact with the surfaces of the second connectors, the third point on the locking member making pressure contact with the surface of the one connector at a fourth point on the latter one connector that is spaced away from the second point, and third means apart from any of said connectors for preventing further rotation of said locking member after the third point on the latter is rotated through the second line and contacts the fourth point on the named one of the second connectors for locking the first and second connectors in this connected relationship.

2. A panel for supporting pairs of elongated mating connectors, one connector pair including first and second mating connectors having elongated bodies, and for selectively locking connector pairs in a connected relationship, comprising a pair of plates that are spaced apart, are parallel to each other, and have surfaces that face each other, each of said facing surfaces having an opening therein;

first means which is a support means extending between said plates for having the first connector attached thereto, the second connector being plugged into the first connector; said first means including a rib extending substantially parallel to first and second connected connectors;

an elongated locking member having opposite ends thereof in associated openings in said plates;

second means including said openings in said plates for rotatably supporting said locking member therebetween for rotation about a first line through said locking member with said locking member adjacent the surface of the second connector that is spaced from the first connector;

the line of rotation which is the first line of said locking member having a second line through a first point on the first line, the second line being substantially normal to the surface of the second connector at a second point on this surface; said locking member also having a third point on the surface thereof that is radially spaced away from said first point; said locking member being rotated about the first line to cause the third point on the former to make pressure contact with the surface of the second connector body at a fourth point on the latter that is spaced away from the second point; and third means for preventing further rotation of said locking member after the third point on the latter is rotated through the second line and contacts the fourth point on the second connector for locking the first and second connectors in this connected relationship; said third means comprising a surface of said rib which contacts said locking member after the latter is rotated.

3. A panel for supporting pairs of elongated mating connectors, one connector pair including first and second mating connectors having elongated bodies, and for selectively locking connector pairs in a connected relationship, comprising a pair of plates that are spaced apart, are parallel to each other, and have surfaces that face each other, each of said facing surfaces having an opening therein with a notch in each opening;

first means which is a support means extending between said plates for having the first connector attached thereto, the second connector being plugged into the first connector;

an elongated locking member having opposite ends thereof which are in associated openings in said plates and having an edge thereof located in said notches;

second means including said openings in said plates for rotatably supporting said locking member therebetween for rotation about a first line through said locking member with said locking member adjacent the surface of the second connector that is spaced from the first connector;

the line of rotation which is the first line of said locking member having a second line through a first point on the first line, the second line being substantially normal to the surface of the second connector at a second point on this surface; said locking member also having a third point on the surface thereof that is radially spaced away from said first point; said locking member being rotated about the first line to cause the third point on the former to make pressure contact with the surface of the second connector body at a fourth point on the latter that is spaced away from the second point; and third means apart from any of said connectors for preventing further rotation of said locking member after the third point on the latter is rotated through the second line and contacts the fourth point on the second connector for locking the first and second connectors in this connected relationship.

4. The panel according to claim 3 wherein the first line which is the line of rotation of said locking member extends through the portion of said locking member that is in said notches.

5. The panel according to claim 4 wherein said third means comprises at least a portion of a surface of at least one of said openings.

6. The panel according to claim 5 wherein said openings extend through said plates, the ends of said locking member extending through the openings and being bent over to form tabs to retain said locking member supported in the openings in said plates during rotation of said locking member.

7. The panel according to claim 6 wherein said plates have slots extending between edges thereof and the openings therethrough for enabling insertion of said locking member into the openings.

* * * * *